United States Patent [19]

Siegl et al.

[11] 4,344,933

[45] Aug. 17, 1982

[54] PHARMACEUTICAL COMPOSITION WITH PROLONGED BRONCHOLYTIC AND TOCOLYTIC ACTIVITY

[75] Inventors: Annemarie Siegl, Linz; Christian Knopp, Graz; Karl Reithmayr, Linz, all of Austria

[73] Assignee: Chemie Linz Aktiengesellschaft, Austria

[21] Appl. No.: 168,139

[22] Filed: Jul. 14, 1980

[30] Foreign Application Priority Data

Jul. 20, 1979 [DE] Fed. Rep. of Germany ....... 2929456

[51] Int. Cl.$^3$ ................... A61K 31/74; A61K 31/135
[52] U.S. Cl. ........................................ 424/79; 424/78; 424/330; 521/32; 521/33
[58] Field of Search ............................ 424/79, 78, 330; 521/32, 33

[56] References Cited

U.S. PATENT DOCUMENTS 3,329,709  7/1967  Schmid et al. ................... 260/570.6

FOREIGN PATENT DOCUMENTS

| 659M | 7/1961 | France . |
|---|---|---|
| 1413851 | 9/1965 | France . |
| 379057 | 8/1964 | Switzerland . |
| 869149 | 5/1961 | United Kingdom . |

OTHER PUBLICATIONS

Wulff, J. of Pharmaceutical Sciences, vol. 54, No. 7, pp. 1058–1060 (1965).

*Primary Examiner*—Leonard Schenkman
*Attorney, Agent, or Firm*—Wenderoth, Lind & Ponack

[57] ABSTRACT

Composition which has a prolonged broncholytic and tocolytic activity and consists of a compound of N,N'-bis-[2-(3',4'-dihydroxyphenyl)-2-hydroxyethyl]-hexamethylenediamine with a polystyrene which is crosslinked with divinylbenzene, contains sulphonic acid radicals as anchor groups and has a degree of crosslinking of 2–5%, and a process for the preparation of this composition by treating the proton form of the resin with an aqueous solution of a bis-salt of the base.

4 Claims, No Drawings

PHARMACEUTICAL COMPOSITION WITH PROLONGED BRONCHOLYTIC AND TOCOLYTIC ACTIVITY

The present invention relates to compositions which have a prolonged broncholytic and tocolytic activity and are derived from N,N'-bis-[2-(3',4'-dihydroxyphenyl)-2-hydroxyethyl]-hexamethylenediamine (hexoprenaline), which is a substance having a $\beta_2$-sympathomimetic action, and to a process for the preparation of the composition and to an agent which has a broncholytic and tocolytic action and releases the active ingredient hexoprenaline slowly and at a uniform rate.

N,N'-Bis[2-(3',4'-dihydroxyphenyl)-2-hydroxyethyl]-hexamethylenediamine and its salts have already been known for a relatively long time as a $\beta_2$-mimetic agent and as an active ingredient in agents having a broncholytic action (U.S. Pat. No. 3,329,709). One advantage of this active compound is that its side-effects on the heart and blood pressure are slight and that the period of action is relatively long. In clinical practice, however, it has been found that a prolongation of the period of action would be desirable.

In order to prolong the period of action of active compounds it has been customary for a long time, if the said active compounds have a basic character, to make use of their adducts with acid ion exchange resins. Phenylalkanolamines, such as noradrenaline, adrenaline and the broncholytic agent isoprenaline have also been converted by reaction with cation exchange resins into so called "retard forms", the ion exchange resins used also including polystyrene which has been crosslinked with divinylbenzene and contain sulphonic acid groups (Swiss Patent Specification No. 379,057). Those resins which are crosslinked to the extent of 7-9% have been particularly preferred, in view of the loading capacity and the release of active compound. Resins with a low degree of crosslinking are hardly suitable for this purpose, since virtually all of the active compound is released too rapidly, for example within the first hour, and there is thus no adequate retardation. Liquid medicinal formulations which contain a resinate of the active ingredient in suspension have also already been proposed; see British Patent Specification No. 869,149. There, a polystyrene resin crosslinked with divinylbenzene, specifically Zeocarb 225, is proposed as the resin component for ephedrine. Though the extent of crosslinkage for Zeocarb 225 is not mentioned there, it can be concluded from French Patent Specification No. 1,413,851, where Zeocarb 225 is listed together with Amberlite IR-120 and Dowex 50 as crosslinked sulfonated polystyrene resin which is capable for making a resinate of ephedrine, that the Zeocarb 225 used has the same extent of crosslinkage of 8% as it is in the case of Amberlite IR-120 and Dowex 50.

However, when this method was used for hexoprenaline it was found that it was not possible to obtain a usable active compound combination using those resins which, for example, gave good characteristics in the case of isoprenaline. Not only was the loading capacity of the resins with 7-9% crosslinking unsatisfactory, being, for example, only 60-65% that for Na in the case of a resin crosslinked to the extent of 8%, the adducts also displayed a brown coloration on prolonged standing, so that they were not suitable for pharmaceutical purposes.

Surprisingly, it has now been found that compositions with a good retard effect and also good stability can be obtained on the basis of hexoprenaline and polystyrenes of the abovementioned type if resins with only 2-5%, and preferably around 4% crosslinking are employed for adduct formation.

Accordingly, the present invention relates to a composition which has a prolonged broncholytic and tocolytic activity consisting of a resinate of a polystyrene which is crosslinked with divinylbenzene, contains sulphonic acid radicals as anchor groups and has a degree of crosslinking of 2-5%, with N,N'-bis-[2-(3',4'-dihydroxyphenyl)-2-hydroxyethyl]-hexamethylenediamine.

Polystyrene resins preferably employed are those which have a degree of crosslinking of 4%, and resins with a degree of crosslinking of 4.5% are also very suitable. For hexoprenaline, the loading capacity of the polystyrene resins employed according to the invention is more than 90% of the capacity for sodium. In the case of fine-grained resins crosslinked to the extent of 4%, it can even be 98%. Coarse-grained resins, for example those from a sieve fraction of 50-100 mesh (U.S. Standard) display a somewhat lower loading capacity than, for example, those of the same type obtained from a sieve fraction of 200-400 mesh (50-100 mesh 91.14% of the Na capacity; 200-400 mesh 98.40% of the Na capacity), the effect of the particle size being as pronounced as this only in the case of the resin with 4% crosslinking, but being much lower in the case of the same resin with only 2% crosslinking (50-100 mesh 91.46% of the Na capacity; 200-400 mesh 93.96% of the Na capacity).

The rate of release of the composition according to the invention is highly advantageous. In tests carried out in vitro it was found that when the polystyrene with 4% crosslinking, which is characterised according to the invention, is used, approximately 80% of the active ingredient hexoprenaline originally present is released after 8 hours. If a resin crosslinked only to the extent of 2% is used, an approximately 80% release is usually already obtained after about 3 hours. The fact that a retention capacity of this level can still be observed in the case of a resin with such a low degree of crosslinking must be evaluated as being particularly surprising. The high stability of the composition according to the invention to oxidation indicates a uniform and complete bonding of the hexaprenaline to the resin.

The composition according to the invention is prepared in a simple manner. After an acid pretreatment has been carried out to ensure that the resin is loaded with protons, the active compound is applied by treating the resin with an aqueous solution of a bis-salt of hexaprenaline. An aqueous solution of the dihydrochloride of hexaprenaline is particularly suitable for this purpose, but other salts, such as, for example, the dihydrobromide, the disulphamate and the diacetate, are also suitable for this purpose.

In principle, it is possible to carry out the treatment of the resin with the aqueous solution in different ways. Thus, for example, the resin can simply be shaken for several hours with an aqueous solution of a salt of hexoprenaline, an N$_2$ atmosphere being used to ensure the exclusion of oxygen, and the batch also has to be protected against light. After loading is complete and after washing with water, the loaded resin can then be dried and used. However, it is also possible, using the so-calld percolation method, to load the resin in a column through which the salt solution is percolated. In this case also, care must be taken to ensure the exclusion of oxygen and protection against light during loading.

After loading has taken place, the compositions according to the invention are stable. Even when stored in an oxygen atmosphere at a temperature of 60° C., the compositions containing resins with 4% crosslinking still show no significant change even after 12 weeks.

The compositions according to the invention are processed, in particular, to medicaments for peroral administration and can be either in the solid form, for example in the form of capsules, dragees or tablets, or in the form of suspensions, for example formulated as a syrup. An individual dose preferably contains 2.4–3.2 mg of the composition, whereby the amount is chosen to correspond to an individual dose of 1.5 mg of hexoprenaline, calculated as dihydrochloride.

The compositions according to the invention can be used for treatment of patients with asthmatic afflictions. The daily doses are for example 1 to 2 dosage units as mentioned above. In cases where the tocolytic activity is used the dosage is different from case to case but may be per example 2 to 4 dosage units per day.

EXAMPLE 1

A commercially available polystyrenesulphonic acid resin with 4% crosslinking with divinylbenzene and a particle size of 200–400 mesh is heated successively with 2 N ammonia solution and 2 N hydrochloric acid, in order to remove low-molecular fractions, the liquid is decanted off and the resin is washed. It is then treated with 1 N hydrochloric acid in order to charge it with protons.

1 g of the resin pre-treated in this way is shaken for 10 hours with a solution of 1.5 g of the dihydrochloride of N,N'-bis-[2-(3',4'-dihydroxyphenyl)-2-hydroxyethyl]-hexamethylenediamine in 100 ml of twice-distilled water under and $N_2$ atmosphere and with protection against light. After filtering off the loaded resin and rinsing with twice-distilled water, the resin is dried in a vacuum drying cabinet.

The precise amount of hexoprenaline bonded to the resin is determined from the difference between the initial concentration and the residual concentration in the solution after loading. It was 1,250 mg, corresponding to 5.07 m equivalents, that is to say 98.40% of the Na capacity of the resin.

The rate of release of the resinate prepared in this way was determined by the so-called replacement closed tube method, that is to say fresh eluent was added to the resinate every hour and the mixture was shaken.

The elution liquid used was artifical gastric juice (pH 1.3) in the first and second hours and artificial intestinal juice (pH=6.5) from the third hour, at a temperature of 37° C.

Gastric juice: 0.199 M; 2 g of NaCl and 80 ml of 1 N HCl are made up to 1,000 ml with twice distilled water.

Intestinal juice: 0.07 M; 10.09 g of $Na_2HPO_4.H_2O$ and 1.76 g of $NaH_2PO_4.12H_2O$ are made up to 1,000 ml with twice distilled water.

The release rates determined in this way are given in the table with follows:

| Hours | Hexoprenaline, % of loading |
|---|---|
| 1 | 36% |
| 2 | 55% |
| 3 | 66% |

-continued

| Hours | Hexoprenaline, % of loading |
|---|---|
| 4 | 70% |
| 5 | 75% |
| 6 | 78% |
| 7 | 80% |
| 8 | 81% |

If a resin of 50–100 mesh is used in place of the resin with a particle size of 200–400 mesh, the loading is 4.24 m equivalent/g, or 1,048 mg/g, that is to say 91.14% of the Na capacity.

If the disulphamate, the diacetate or the dihydrobromide is employed in place of the dihydrochloride of N,N'-bis-[2-(3',4'-dihydroxyphenyl)-2-hydroxyethyl]-hexamethylenediamine and in other respects the procedure is as indicated above, the loading, when the resin with a particle size of 200–400 mesh is used, is 4.98 m equivalent/g, that is to say 96.7% of the Na capacity, when the disulphamate is used, 4.92 m equivalent/g, that is to say 95.5% of the Na capacity, when the diacetate is used and 4.95 m equivalent/g, that is to say 96.1% of the Na capacity, when the dihydrobromide is used.

EXAMPLE 2

1 g of polystyrenesulphonic acid resin with 2% crosslinking with divinylbenzene and a particle size of 200–400 mesh, which has been pre-treated in accordance with the method indicated in Example 1, is suspended in 200 ml of distilled water, the suspension is introduced into a column and 100 ml of an aqueous solution of hexoprenaline. 2 HCl with a hexoprenaline concentration of 1.5% by weight are then introduced into the column, under an $N_2$ atmosphere and with protection against light, a drip rate of 1 ml/minute being used. The resin is then rinsed with twice-distilled water and taken from the column, and dried as in Example 1.

The loading was 4.98 m equivalent/g, or 1,229.6 mg/g, that is to say 93.96% of the Na capacity.

The release rate, determined by the method of Example 1, was:

| Hours | Hexoprenaline, % of loading |
|---|---|
| 1 | 55% |
| 2 | 72% |
| 3 | 80% |
| 4 | 82% |
| 5 | 85% |
| 6 | 86% |
| 7 | 87% |
| 8 | 88% |

EXAMPLE 3

From 1 g of a polystyrene sulphonic acid resin with 4.5% crosslinking with divinylbenzene and a particle size of 200–400 mesh the resinate of hexoprenaline is produced as described in example 1.

The loading thereby obtained is 4.93 m equivalent/g or 1,216.4 mg/g, that is to say 96.66% of the Na capacity of the resin.

EXAMPLE 4

A tablet was prepared from a hexoprenaline resinate prepared by the method of Example 1, using the following constituents:

| Hexoprenaline resinate | 2.4 mg |
|---|---|
| Lactose | 95.6 mg |
| Maize starch | 23.0 mg |
| Collidone | 7.0 mg |
| Glycerol palmitostearate | 2.0 mg |
| | 130.0 mg |

The tablet has an active ingredient content of 1.5 mg of hexoprenaline calculated as dihydrochloride.

The tablet prepared in this way can also be coated with lacquer.

EXAMPLE 5

Granules are prepared from the constituents named in Example 3 and these are filled into a size 4 capsule.

EXAMPLE 6

50.0 g of sucrose are boiled with 48.54 g of sterile water to give a syrup, and at the end of the boiling process 0.06 g of methyl p-hydroxybenzoate and 0.03 g of propyl p-hydroxybenzoate, both dissolved in 1 ml of ethanol, are added. After cooling, 1.2 g of methylcellulose and 0.15 g of microcrystalline cellulose are mixed in and worked in under the action of shearing forces. 0.012 g of the hexoprenaline resinate prepared according to Example 1 are then mixed in. This gives 100 g of a syrup which is suitable for peroral administration.

What we claim is:

1. A pharmaceutical complex with prolonged broncholytic and tocolytic activity consisting of a resinate prepared by reacting N,N'-bis-[2-(3',4'-dihydroxyphenyl)-2-hydroxyethyl]-hexamethylenediamine with a polystyrene resin which is cross-linked with divinylbenzene to a degree of 2–5% and contains sulfonic acid radicals as anchor groups.

2. The pharmaceutical complex according to claim 1 wherein the degree of cross-linking of said polystyrene is about 4%.

3. A pharmaceutical composition for peroral administration having broncholytic and tocolytic activity comprising a broncholytically or tocolytically effective amount of the complex according to claim 1 and a pharmaceutically acceptable carrier.

4. The pharmaceutical composition for peroral administration according to claim 3 which is in a shaped dosage unit wherein the amount of said complex corresponds to 1.5 mg of N,N'-bis-[2-(3',4'-dihydroxyphenyl)-2-hydroxyethyl]-hexamethylenediamine-dihydrochloride.

* * * * *